United States Patent [19]

Archibald et al.

[11] Patent Number: 4,985,438
[45] Date of Patent: Jan. 15, 1991

[54] PYRIDYL-AND/OR PYRIDOYL-(PIPERID-4-YL) UREAS AND ANALOGUES THEREOF

[75] Inventors: John L. Archibald, Farnham Royal; Terence J. Ward, Maidenhead, both of United Kingdom

[73] Assignee: John Wyeth & Brother, Limited, Maidenhead, England

[21] Appl. No.: 259,653

[22] Filed: Oct. 19, 1988

Related U.S. Application Data

[60] Division of Ser. No. 929,964, Nov. 12, 1986, Pat. No. 4,806,552, which is a continuation-in-part of Ser. No. 781,832, Sep. 30, 1985, Pat. No. 4,722,930, which is a division of Ser. No. 545,802, Oct. 26, 1983, Pat. No. 4,563,466, which is a continuation-in-part of Ser. No. 366,266, Apr. 7, 1982, Pat. No. 4,426,387, which is a continuation of Ser. No. 238,381, Feb. 25, 1981, abandoned.

[30] Foreign Application Priority Data

Mar. 1, 1980 [GB] United Kingdom ............... 8007048
Aug. 22, 1980 [GB] United Kingdom ............... 8027435
Nov. 15, 1985 [GB] United Kingdom ............... 8528235

[51] Int. Cl.$^5$ ................. A61K 31/445; C07D 401/12; C07D 401/00
[52] U.S. Cl. .................... 514/307; 514/312; 514/314; 546/139; 546/146; 546/148; 546/152; 546/153; 546/155; 546/156; 546/174; 546/175
[58] Field of Search ............. 546/139, 146, 148, 152, 546/174, 175, 153, 155, 156; 514/307, 314, 312

[56] References Cited

U.S. PATENT DOCUMENTS

| | | | |
|---|---|---|---|
| 4,073,790 | 2/1978 | Archibald et al. | 546/224 |
| 4,177,279 | 12/1979 | Archibald et al. | 424/267 |
| 4,199,590 | 4/1980 | Ward | 424/267 |
| 4,209,521 | 6/1980 | Archibald et al. | 424/267 |
| 4,235,915 | 11/1980 | Archibald et al. | 424/267 |
| 4,281,132 | 7/1981 | Ward | 546/224 |
| 4,425,343 | 1/1984 | Sakata et al. | 514/312 |
| 4,569,933 | 2/1986 | Cornu et al. | 514/314 |
| 4,704,390 | 11/1987 | Caprathe et al. | 514/307 |
| 4,778,802 | 10/1988 | Archibald et al. | 514/314 |

FOREIGN PATENT DOCUMENTS

| | | |
|---|---|---|
| 0002886 | 11/1979 | European Pat. Off. |
| 0007525 | 2/1980 | European Pat. Off. |
| 2545501 | 7/1976 | Fed. Rep. of Germany |
| 48-7110 | 3/1973 | Japan |
| 77-85174 | 7/1977 | Japan |
| 2034305 | 6/1978 | United Kingdom |

OTHER PUBLICATIONS

Carey and Sundberg, Advanced Organic Chomistry, Part A, (Plenum Press, New York) 1924 pp. 496-7.
Foye, Principals of Medicinal Chemistry (Lea and Febiger Philadelphia, 1981) p. 34.
Irikura et al., Chem. Abst., 78, 159433a: (1973).
Arimura, Katsuo et al., Chem. Abst., 88, 22640c, (1978).

*Primary Examiner*—Mukund J. Shah
*Assistant Examiner*—E. C. Ward
*Attorney, Agent, or Firm*—Arthur G. Seifert

[57] ABSTRACT

The invention concerns the preparation of compounds of formula

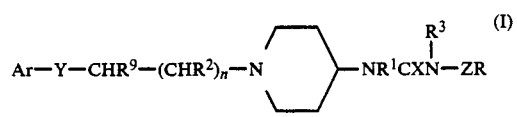

and acid addition and quaternary ammonium salts thereof, wherein the dotted line represents an optional bond, Ar represents a ring system of formula

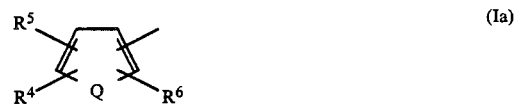

in which Q is O, S, —CR$^7$=CR$^8$—, —N=CR$^8$— and —N=N—; R$^4$, R$^5$ and R$^6$; and R$^7$ and R$^8$ when present, each represent hydrogen or a substitutent selected from lower alkyl, lower alkenyl, lower alkoxy, NO$_2$, NH$_2$, haloloweralkyl, hydroxyloweralkyl, aminoloweralkyl, substituted amino, halogen, loweralkoxycarbonyl, cyano, CONH$_2$ and hydroxy; and additionally either R$^4$ and R$^5$ when adjacent or R$^6$ and R$^8$ when adjacent, together with the carbon atoms to which they are attached also represent a fused five or six membered carbocyclic or heterocyclic ring optionally carrying one or more substituents as defined above; R is an optionally substituted aryl or heteroaryl radical or a cycloalkyl radical containing 5 to 7 carbon atoms; R$^1$, R$^2$, R$^3$ and R$^9$ are each hydrogen or a lower alkyl group; n is 0 or 1; X is =O, =S or =NH; Y is —O— or a direct bond and Z is —CO— or —CH$_2$—, with the proviso that when Ar is unsubstituted phenyl and R$^9$ is hydrogen then y is —O—. The compounds of formula I exhibit psychotropic activity and are useful as antidepressants.

20 Claims, No Drawings

PYRIDYL-AND/OR PYRIDOYL-(PIPERID-4-YL) UREAS AND ANALOGUES THEREOF

This invention relates to new piperidine derivatives, to processes for preparing them and to pharmaceutical compositions containing them. This application is a divisional application of our co-pending application Ser. No. 929,964, filed on Nov. 12, 1986 (now U.S. Pat. No. 4,806,552 issued on Feb. 21, 1989). Said application Ser. No. 929,964 is a continuation-in-part of our co-pending application Ser. No. 781,832, filed on Sept. 30, 1985 (now U.S. Pat. No. 4,722,930, issued on Feb. 2, 1988). Said application Ser. No. 781,832 is, in turn, a division application of co-pending application Ser. No. 545,802, filed Oct. 26, 1983 (now U.S. Pat. No. 4,563,466, issued on Jan. 7, 1986). Said Ser. No. 545,802, is, in turn, a continuation-in-part of co-pending application Ser. No. 366,266, filed on Apr. 7, 1982 (now U.S. Pat. No. 4,426,387, issued on Jan. 17, 1984). Said Ser. No. 366,266 is, in turn, a continuation of co-pending application Ser. No. 238,381, filed on Feb. 25, 1981 (now abandoned).

More particularly this invention provides piperidino ureas, thioureas and guanidines which exhibit pharmaceutical activity especially psychotropic activity in standard pharmacological test procedures, and are potentially useful as anti-depressants. In general the compounds are specific inhibitors of 5-hydroxytryptamine re-uptake in vitro and in vivo, and therefore may also be useful in any other therapeutic applications where such pharmacological specificity may be beneficial.

The invention provides compounds of formula:

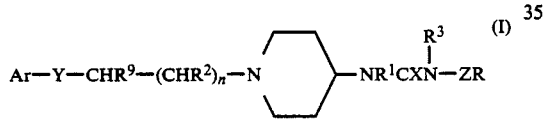

and acid addition and quaternary ammonium salts thereof, wherein the dotted line represents an optional bond, Ar represents a ring system of formula

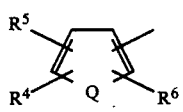

in which Q is O, S, $-CR^7=CR^8-$, $-N=CR^8-$ and $-N=N-$; $R^4$, $R^5$ and $R^6$, and $R^7$ and $R^8$ when present, each represent hydrogen or a substituent selected from lower alkyl, lower alkenyl, lower alkoxy, $NO_2$, $NH_2$, haloloweralkyl, hydroxyloweralkyl, aminoloweralkyl, substituted amino, loweralkoxycarbonyl, CN, halogen, $CONH_2$ and hydroxy; and additionally either $R^4$ and $R^5$ when adjacent or $R^6$ and $R^8$ when adjacent, together with the carbon atoms to which they are attached also represent a fused five or six membered carbocyclic or heterocyclic ring optionally carrying one or more substituents as defined above; R is an optionally substituted aryl or heteroaryl radical or a cycloalkyl radical containing 5 to 7 carbon atoms; $R^1$, $R^2$, $R^3$ and $R^9$ are each hydrogen or a lower alkyl group; n is 0 or 1; X is =O, =S or =NH; Y is $-O-$ or a direct bond and Z is $-CO-$ or $-CH_2-$, with the proviso that when Ar is unsubstituted phenyl and $R^9$ is hydrogen then Y is $-O-$.

The term 'lower' as used in connection with alkyl or alkoxy groups means that such groups contain 1 to 6 carbon atoms especially 1 to 4 carbon atoms. 'Substituted amino' includes groups such as alkyl- or dialkylamino, acylamino e.g. lower alkylcarbonylamino, ureido or sulphonylamino, e.g. lower alkylsulphonylamino or di-lower-alkylsulphonylamino.

Examples of lower alkyl groups are methyl, ethyl n-propyl, isopropyl, t-butyl, neo-pentyl and n-hexyl. Examples of lower alkoxy groups are methoxy, ethoxy, isopropoxy, butoxy and hexoxy. Examples of cycloalkyl groups are cyclohexyl and cyclopentyl.

'Hydroxyloweralkyl' includes groups such as $HO(CH_2)_m-$ where m is 1 to 4, e.g. hydroxymethyl or hydroxyethyl.

Examples of lower alkylamino and di-lower-alkylamino groups are MeNH—, EtNH—, dimethylamino, isopropylamino and butylamino.

Examples of lower alkenyl groups are vinyl, propenyl, but-1-enyl and but-2-enyl.

Examples of haloloweralkyl groups are chloroethyl and trifluoromethyl.

'Aminoalkyl' includes groups such as $NH_2(CH_2)_m-$ where m is 1 to 4, e.g. aminomethyl, aminoethyl.

Examples of lower alkoxycarbonyl groups are methoxy-and ethoxycarbonyl.

Preferred halogen substituents are chlorine and bromine.

Examples of the group Ar when Q is O or S are

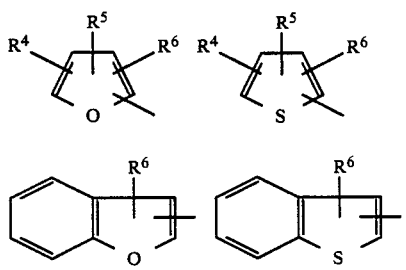

especially furan-2-yl, thiophen-2-yl, benzo[b]furan-3-yl, benzo[b]-thiophen-3-yl. Examples of Ar when Q is $-CR^7=CR^8-$ are

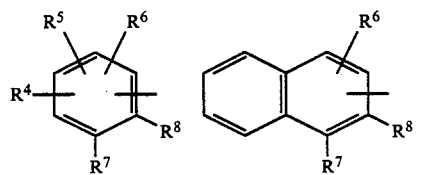

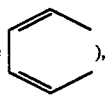

(i.e. $R^4$ and $R^5$ are )

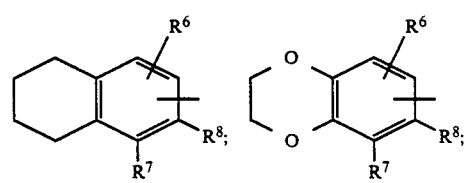

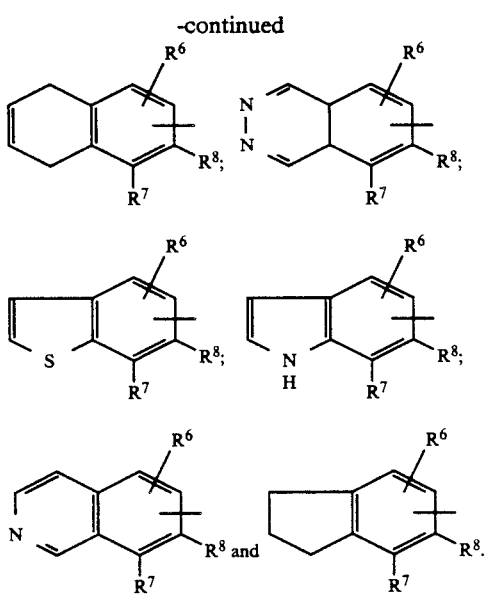

Examples of Ar when Q is —N=CR$^8$— are

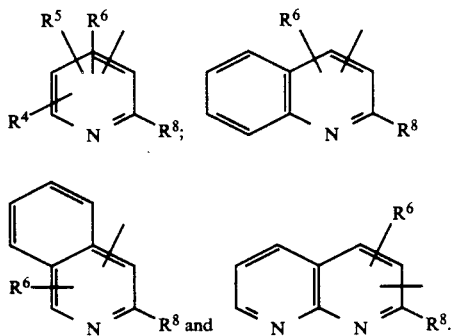

When Q is —N=N— examples are

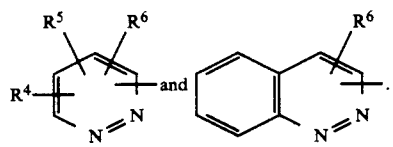

When monosubstituted phenyl or pyridyl the group Ar may be for example 4-t-butylphenyl, 4-cumenyl, 4-n-butoxyphenyl, 4-nitrophenyl, 4-dimethylaminophenyl, 3-vinylphenyl, 3-methylpyrid-2-yl, 4-methylpyrid-2-yl, 4-methylpyrid-3-yl, 4-chloropyrid-2-yl, 2-methylpyrid-4-yl or 2-bromopyrid-4-yl. When multi-substituted phenyl or pyridyl the group Ar may be for example 3,4-dichlorophenyl; 3,4,5-trimethylphenyl; 3,4,5-trimethoxyphenyl; 3,4-dichloro-2-methylphenyl; 2,3-diethylphenyl, 3-methyl-4-vinylphenyl, 2,4-dichloropyrid-6-yl, 2,4-dimethylpyrid-6-yl. Examples of Ar when phenyl having a fused 5- or 6-membered carbocyclic or heterocyclic ring are naphth-1-yl; naphth-2-yl; benzo[1,4]dioxan-6-yl; 3,4-methylene-dioxyphenyl; 1,2,3,4-tetrahydronaphth-6-yl; 1,4-dihydronaphth-6-yl; benzo[b]thiophen-6-yl; indol-6-yl; benzo[b]furan-6-yl; quinol-6-yl and quinol-5-yl. Examples of Ar when pyridyl having a fused 5 or 6 membered carbocyclic or heterocyclic ring are quinol-4-yl, quinol-2-yl, 5,6,7,8-tetrahydro-quinol-4-yl or 5,6,7,8-tetrahydro-quinol-2-yl. Examples of such groups when substituted in the fused ring are 6-methoxy-naphth-2-yl, 7-methoxy-naphth-2-yl and 4-methylnaphth-2-yl. Preferred fused heterocyclic 'Ar' rings have oxygen, nitrogen or sulphur as heteroatom(s).

The group R is exemplified by aryl radicals such as phenyl which can be substituted for example by the substituents listed for R$^4$, e.g. methyl (such as 4-methyl) ethyl, propyl, nitro (such as 3- or 4-nitro), hydroxy (such as 4-hydroxy), methoxy, ethoxy, fluorine, bromine, or chlorine (such as 3,4-dichloro). Heteroaryl radicals for R include thienyl (e.g. thien-2 or 3-yl), furyl (e.g. fur-2 or 3-yl) and pyridyl (e.g. pyrid-2-yl, pyrid-4-yl, pyrid-3-yl), which radicals may be substituted as described above for the phenyl radical Ar.

Preferred values for Ar are

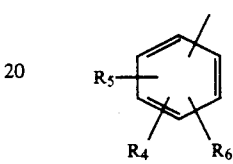

in which
R$_4$, R$_5$, and R$_6$, when present, independently, are hydrogen, lower alkyl, lower alkenyl, lower alkoxy, hydroxy, hydroxyloweralkyl, fluoro, bromo, chloro, chloroloweralkyl, fluoroloweralkyl, amino, aminoloweralkyl, substituted amino, loweralkoxycarbonyl, nitro, cyano, or amido, or R$_4$ and R$_5$, when adjacent, together with the carbon atoms to which they are attached also are fused five or six member carbocyclic ring with 0-2 double bonds and optionally carrying one or two substituents as defined above for said R$_4$ and R$_5$.

Other preferred values for Ar are heterocyclic systems containing one N, O or S heteroatom, or two identical N, O or S heteroatoms, in one or two 5 or 6 membered rings, the ring bonded to Y being an aromatic ring other than a 5-membered ring containing nitrogen, said system optionally carrying one or two substituents from lower alkyl, lower alkenyl, lower alkoxy, hydroxy, hydroxyloweralkyl, fluoro, bromo, chloro, chloroloweralkyl, fluoroloweralkyl, amino, aminoloweralkyl, substituted amino, loweralkoxycarbonyl, nitro, cyano, or amido.

Preferred values for R are phenyl or phenyl substituted by one or two of the same substituents selected from lower alkenyl, lower alkoxy, lower alkyl, hydroxy, hydroxyloweralkyl, fluoro, bromo, chloro, chloroloweralkyl, fluoroloweralkyl, amino, aminoloweralkyl, substituted amino, loweralkoxycarbonyl, nitro, cyano or amido.

Other preferred values for R are thienyl, furyl or pyridyl substituted by one or two of the same substituents selected from loweralkyl, lower alkenyl, lower alkoxy, hydroxy, hydroxyloweralkyl, fluoro, bromo, chloro, chloroloweralkyl, fluoroloweralkyl, amino, aminoloweralkyl, substituted amino, loweralkoxycarbonyl, nitro cyano or amido.

Most preferably Ar is phenyl substituted by one or more alkyl or alkoxy groups of 2 or more carbon atoms, e.g. 4-ethylphenyl, 3,4 dimethylphenyl, 3,4-dimethoxyphenyl; phenyl having a fused 5 or 6 membered carbocyclic ring, e.g. naphth-1-yl, naphth-2-yl, such groups being optionally substituted by lower alkyl, lower alkoxy, halogen, nitro, trifluoromethyl, amino, lower alkylamino (e.g. methylamino) diloweralkylamino (e.g. dimethylamino) and cyano.

Preferably n is O, $R^9$ is hydrogen or methyl and $R^1$ is hydrogen. Preferably X is oxygen.

Preferably Z is —CO— and R is phenyl or phenyl substituted in the 4-position by lower alkoxy, e.g. methoxy.

Y is preferably a direct bond.

When Z is —CH$_2$—, R is preferably phenyl.

Preferred compounds of the invention are 1-benzoyl-3-[1-(naphth-2-ylmethyl)piperid-4-yl]urea; 1-benzoyl-3-[1-(naphth-1-ylmethyl)piperid-4-yl]urea; 1-benzoyl-3-[1-(4-isopropylbenzyl)piperid-4-yl]urea; 1-benzoyl-3-[1-(5,6,7,8-tetrahydronaphth-2-ylmethyl)piperid-4-yl]urea; 1-benzoyl-3-[-(3,4-dimethylbenzyl)piperid-4-yl]urea; 1-benzoyl-3-[1-(indan-5-ylmethyl)piperid-4-yl]urea; 1-benzoyl-3-[1-(1-(naphth-2-yl)ethyl)piperid-4-yl]urea; N-[[[1-[(6-Fluoro-2-naphthalenyl)methyl]-4-piperidinyl]amino]carbonyl]-3-pyridinecarboxamide; and N-[[[1-[(6-Fluoro-2-naphthalenyl)methyl]-4-piperidinyl]amino]carbonyl]-4-pyridinecarboxamide.

Examples of acid addition salts are those formed from inorganic and organic acids and in particular pharmaceutically acceptable acid addition salts from such as the hydrochloride, hydrobromide, hydroiodide, sulphate, nitrate, phosphate, sulphonate (such as the methanesulphonate and p-toluenesulphonate), acetate, maleate, citrate, fumarate, tartrate, malonate and formate.

Compounds of formula I were tested for psychotropic activity by their ability to inhibit p-chloroamphetamine (pCA) induced hyperactivity and/or by their ability to inhibit 5-hydroxytryptamine (5-HT) uptake in brain slices.

The following test procedure was used to test for ability to inhibit p-chloroamphetamine induced hyperactivity.

Three groups of 4 female mice (20-24 g) receive the test compounds (50 mg/kg po) and a fourth group the requisite volume of vehicle. Thirty minutes later all the animals are given 20 mg/kg p-chloroamphetamine (pCA) ip. The grouped mice are placed immediately in square plastic cages in activity monitors and their motor activity recorded over the period 10-30 minutes post pCA. This procedure is repeated three more times so that four groups of mice are used per treatment and each activity monitor is used with all treatments in turn. The inhibition of pCA induced hyperactivity is calculated thus:

$$\frac{C - T}{C} 100\%$$

where
C=mean activity of control groups 10-30 minutes post pCA.
T=mean activity of treated groups 10-30 minutes post pCA.

This test is used as an in vivo screen for detection of 5-hydroxytryptamine uptake inhibitors.

Compounds giving >50% inhibition are considered of special interest. In such a test the following compounds were particularly active:

| Compound | % Inhibition of pCA induced hyperactivity |
|---|---|
| 1-Benzoyl-3-[1-(naphth-2-ylmethyl)-piperid-4-yl]urea | 67.5% |
| 1-Benzoyl-3-[1-(naphth-1-ylmethyl)-piperid-4-yl]urea | 56.4% |
| 1-Benzoyl-3-[1-(4-isopropylbenzyl)-piperid-4-yl]urea | 49% |
| 1-Benzoyl-3-[1-(5,6,7,8-tetrahydro-naphth-2-ylmethyl)piperid-4-yl]urea | 69.4%, 73.5% |
| 1-Benzoyl-3-[1-(3,4-dimethylbenzyl)-piperid-4-yl]urea | 68.9% |
| 1-Benzoyl-3-[1-(indan-5-ylmethyl)-piperid-4-yl]urea | 59.3% |
| 1-Benzoyl-3-[1-(1-naphth-2-yl)ethyl]-piperid-4-yl]urea | 71.7% |
| 1-Benzoyl-3-[1-(4-ethylbenzyl)-piperid-4-yl]urea | 72.9% |

Compounds of formula I were tested for ability to inhibit 5-hydroxytryptamine (5-HT) uptake in brain slices using the following procedure:

The effects of test compound on the neuronal uptake of 5-hydroxytryptamine into slices of cerebral cortex prepared from rat brain is determined according to the method described by Snyder, Green and Hendley, Kinetics of H$^3$-norepinephrine accumulation into slices from different regions of the rat brain (J. Pharm. exp. Therap. 164: 90-102) (1968). Concentration-response curves for the test compound and for the standard agent, imipramine, are obtained. The potency of the test compound is expressed in proportion to that of imipramine. Thus, the potency ratio for the test compound -

$$\frac{\text{Molar concentration of imipramine giving 50\% inhibition of 5HT uptake}}{\text{Molar concentration of test drug giving 50\% inhibition of 5HT uptake}}$$

Compounds not achieving 50% inhibition are considered inactive.

In such a test the compound 1-benzoyl-3-[1-(naphth-2-ylmethyl)piperid-4-yl]urea above was particularly active having a potency ratio of 8.8 (imipramine=1.0).

In vivo 5-HT uptake inhibition was also demonstrated for compounds of the invention by a procedure involving 5-hydroxy-L-tryptophan (5-HTP) induced behavioural syndrome. Mice given a high dose of 5-HTP exhibit a behavioural syndrome consisting of tremor, hind limb abduction, lateral head weaving and forepaw treading. In addition to these signs rats also exhibit head twitching and circling behaviour. In the following experiments the syndrome was said to be present if mice exhibited at least 3 and rats at least 4 of these signs. When animals are given a low dose of 5-HTP, which does not itself produce the syndrome, it can be produced by pretreatment with 5-HT uptake inhibitors. Thus, this test can be used as an indication of in vivo 5-HT uptake inhibition.

(a) Dose/response study in mice

Groups of 12 (2 subgroups of 6) female mice (18-22 g) were used per dose, each group being housed in a separate cage for the duration of the experiment. Mice were dosed p.o. with either test compound or vehicle (0.5% HPMC) and 30 minutes later received a threshold dose of 5-HTP (80 mg/kg i.p.) and were placed in perspex cylinders (12" diameter). After a further 20 minutes the mice were observed for 5 minutes for the presence or absence of the syndrome.

The dose that produced the syndrome in 50% of the mice was calculated using the method of Litchfield and Wilcoxon, J. Pharm. Exp. Ther. 96, 99–113 (1949).

(b) Dose/Response study in rats

Groups of 6 male rats (150 g) were dosed with test compound suspended in HPMC. Thirty minutes later 5-HTP (70 mg/kg i.p.) was given and the number of signs/rat recorded between 20 and 35 minutes post 5-HTP. Linear regression analysis of the results was performed and the $ED_{50}$ calculated from this.

The results found for 1-benzoyl-3-[1-(naphth-2-ylmethyl)piperid-4-yl]urea (A) and for the antidepressant clomipramine are shown below:

| Compound | $ED_{50}$ values for potentiation of 5-HTP syndrome in: | |
| --- | --- | --- |
|  | Mice (mg/kg po) | Rats (mg/kg ip) |
| A | 7.2 | 5.3 |
| clomipramine | 18 | 39.2 |

In a preferred embodiment this invention provides a compound of formula IA

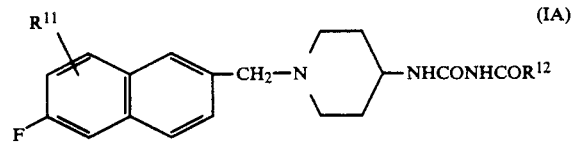

(IA)

or salts thereof, wherein $R^{12}$ is 3- or 4-pyridyl, $R^{11}$ is hydrogen or fluorine, and is bonded to any of the vacant naphthalene ring positions, e.g. 5- or 7-. In formula IA, $R^{11}$ is preferably hydrogen in which case the compound is N-[[[1-[(6-fluoro-2-naphthalenyl)methyl]-4-piperidinyl]amino]carbonyl]-3-pyridinecarboxamide (C) or N-[[[1-[(6-fluoro-2-naphthalenyl)methyl]-4-piperidinyl]amino]carbonyl]-4-pyridine carboxamide (D).

Representative compounds of formula IA were tested for their ability to inhibit pCA induced syndrome in rats by the standard procedure described below:

Inhibition of p-chloroamphetamine (pCA)-induced stereotypy

Vehicle or drug (5 dose levels) were administered p.o. to six groups of 6–8 male Sprague-Dawley rats (300–400 g) followed, 90 minutes later, by pCA (10 mg/kg i.p.). The animals were then placed in individual observation chambers and, 30 minutes after pCA administration, the intensity of the pCA-induced 5-HT syndrome was assessed according to the following scoring system:

| hind-limb abduction head-weaving fore-paw treading | } 0, 1, 2 or 3 according to severity |
| --- | --- |
| tremor | 0 (absent) or 1 (present) |

Therefore, the maximum score for each animal was 10.

The inhibition of pCA induced stereotypy is calculated for each dose level as follows:

$$\frac{C - T}{C} \ 100\%$$

where
C = control group total score at 30 minutes post pCA.
T = group total score of treated group at 30 minutes post pCA.

For each dose a % effect is calculated.

The results obtained from the tests using 5 different dose levels of the drug allow the $ED_{50}$ value (i.e. the dose required to produce 50% inhibition of pCA induced stereotypy) to be calculated.

In the aforementioned test the representative compounds C and D antagonised pCA-induced stereotypy in a dose-dependent manner and gave the following $ED_{50}$ values:

| Compounds of Formula I | $ED_{50}$ (mg/kg) |
| --- | --- |
| C | 2.5 |
| D | 3.8 |

The test was carried out using the free bases for compound C. Compound B was tested in the form of the succinate salt and the results corrected for amount of active material.

At 50 mg/kg the compound C showed a 99% inhibition of syndrome.

The compound (C) was also tested for its ability to potentiate 5-hydroxy-L-tryptophan induced behavioural syndrome in rats. The test procedure is described below Potentiation of 5-hydroxytryptophan (5-HTP)-induced behaviour Groups of 10 male Sprague-Dawley rats (310–360 g) were dosed p.o. with vehicle or drugs. Ninety minutes later 5-HTP (50 mg/kg s.c.) was administered and the animals placed in individual observation chambers (peripheral decarboxylation was prevented by 25 mg/kg i.p. carbidopa administered 60 minutes before 5-HTP). Head shakes were counted over the period 30–45 minutes after 5-HTP and the intensity of the 5-HT syndrome was scored immediately afterwards using the system described for the pCA procedure above. Percentage potentiation of syndrome was calculated as follows:

| hind-limb abduction head-weaving tremor | 0, 1, 2 or 3 according to severity |
| --- | --- |
|  | 0 (absent) or 1 (present) |
| fore-paw treading | |
| Percentage potentiation was calculated from the following: | |
| $\frac{\text{test score} - \text{control score}}{\text{maximum possible score} - \text{control score}} \times 100$ | |

In this test the compound (C) as the citrate salt had an $ED_{50}$ value of 5.0 mg/kg (corrected for amount of base).

In vitro tests have shown that compounds of formula IA also have a marked degree of selectivity in inhibiting uptake of 5-HT into rat brain synaptosomes relative to uptake of $^3H$ noradrenaline. The test procedure involved obtaining synaptosomal preparations from male Sprague Dawley rats according to the method of Grey and Whittaker* as modified by Wood and Wyllie**. Aliquots of the synaptosomal preparation were then incubated with tritrated noradrenaline (NA) or 5-HT at a temperature of 37° C. for 4 minutes. The active synaptosomal accumulation of labelled substrate was measured by filtration and scintillation counting. The effect at a range of concentrations of test compound enabled $IC_{50}$ values and selectivity ratios to be calculated. The values found for compound A are shown below:

| Compound | $IC_{50}$ (μM) 5-HT uptake | NA | Selectivity Ratio |
|---|---|---|---|
| A | 0.044 | 20.0 | 455 |

* Grey and Whittaker, - J. Anat. 96 79 (1962)
** Wood and Wyllie, J. Neurochemistry, 37, 795 (1981)

This invention also provides processes for preparing compounds of formula I or acid addition or quaternary ammonium salts thereof. In general the compounds of formula I are prepared by building up the molecule from the appropriate starting materials by known reactions. Accordingly a first process for preparing a compound of formula I comprises reacting a compound of formula II

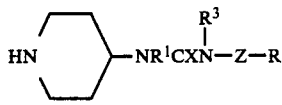
(II)

wherein the dotted line, R, $R^1$, $R^3$, Z and X are as defined in connection with formula I, with a compound of formula III

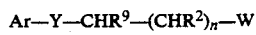 (III)

wherein Ar, Y, n, $R^2$ and $R^9$ are as defined above and W represents a leaving group, such as halogen, (e.g. chlorine, bromine or iodine), an organic sulphonyloxy radical (e.g. tosyloxy, mesyloxy), or a radical of formula $-OSO_2OR$ where R is W—A—, i.e. a sulphate.

The reaction is preferably carried out in the presence of base, e.g. potassium carbonate, triethylamine; otherwise the reaction may be carried out by heating in the presence of an inert solvent, e.g. toluene.

A second general process for preparing compounds of formula I wherein X is O or S and $R^3$ is hydrogen comprises reacting a compound of formula

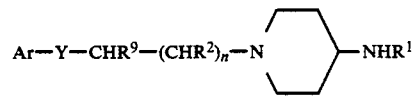 (IV)

wherein Ar, Y, $R^1$, $R^2$, $R^9$ and n are as hereinbefore defined with a compound of formula

 (V)

wherein R and Z are as hereinbefore defined and X is O or S. Such a reaction can be effected at room temperature. The starting materials of formula (IV) wherein $R^1$ is hydrogen may be prepared by methods described in our U.K. Patent Specification No. 1,345,872. The starting materials of formula IV wherein $R^1$ is lower alkyl may be prepared by alkylating corresponding compounds of formula IV wherein $R^1$ is hydrogen, or by methods analogous to those described in Specification No. 1,345,872.

A further process for preparing compounds of formula I comprises reacting a compound of formula IV as defined hereinbefore with a compound of formula

wherein R, $R^3$ and Z are as defined above and X is as defined above and if desired converting the product to an acid addition salt.

This process may be performed in the absence of solvent but is usually carried out by heating the reactants in the presence of a suitable inert organic solvent, for example toluene, pyridine, xylene, chlorobenzene, dimethylformamide or dioxan. Pyridine is the preferred solvent. Often it is convenient to reflux the reactants in the solvent until the reaction is complete. High yields e.g. 80-90% can be obtained. Preferably the solvent has a boiling point greater than 100° C.

It is preferred to use equimolar amounts of the reactants.

A still further process for preparing compounds of formula I as hereinbefore defined wherein Z is —CO— comprises acylating a compound of formula

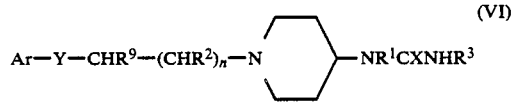 (VI)

wherein the dotted line, Ar, X, Y, $R^2$, $R^3$, $R^9$, n and $R^1$ are as hereinbefore defined with an acylating agent containing the group —COR. Examples of acylating agents are reactive derivatives of acids of formula RCOOH such as the acid halides (e.g. chloride, bromide) and the anhydride and activated esters as used in peptide chemistry. Other methods of acylation are well known in the art such as those employing coupling agents such as carbodiimides, e.g. dicyclohexylcarbodiimide.

Compounds of formula VI may be prepared by hydrolysis of compounds of formula I wherein Z is —CO—.

Compounds of formula I may also be prepared by reducing a compound of formula VII or VIII

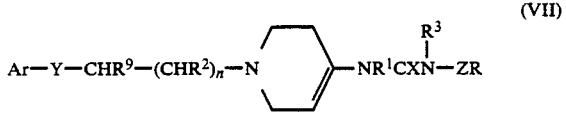 (VII)

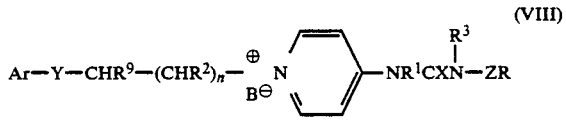 (VIII)

in which formulae Z, X, Ar, Y, n, R, $R^1$, $R^2$, $R^3$ and $R^9$ are as hereinbefore defined and $B^\ominus$ represents an anion, e.g. a halide ion. For example catalytic hydrogenation when X=O, e.g. in the presence of Raney nickel or platinum catalyst gives piperidine compounds of formula I. The reduction may also be effected by a process described and claimed in our U.K. Patent Specification No. 1542137. Such a reduction process employs an alkali metal borohydride in a secondary alkanol having 3–5 carbon atoms, e.g. isopropanol. Alternatively reduction of compounds of formula VIII using an alkali metal borohydride in methanol gives dehydropiperidine compounds of formula I.

Yet a further process for preparing a compound of formula I comprises reacting a compound of formula

wherein Ar, Y, n, $R^2$ and $R^9$ are as hereinbefore defined with a compound of formula II, when X=O, in the presence of a catalyst, e.g. a nickel catalyst such as Raney nickel.

Compounds of formula I wherein X is =O or =NH may also be prepared by treating a corresponding compound of formula (X)

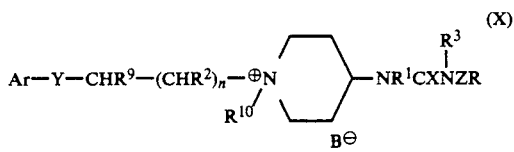

wherein the dotted line Ar, Y, R, $R^1$, $R^2$, $R^3$, $R^9$ and $B^\ominus$ are as hereinbefore defined, n is 1 and $R^{10}$ is an organic quaternizing group which can be removed under mild conditions, e.g. by hydrogenolysis, that do not affect the rest of the molecule. For example, when $R^{10}$ is an arylmethyl radical, such as benzyl, hydrogenolysis under standard conditions, e.g. using an appropriate catalyst such as a palladium on carbon, platinum or nickel catalyst, gives compounds of formula I. Methods for effecting this reaction are given in our U.K. Patent Specification No. 1,399,608. Suitably solvents include alkanols such as methanol.

Starting materials of formula X may be prepared by reacting a compound of formula III as defined above with a compound of formula

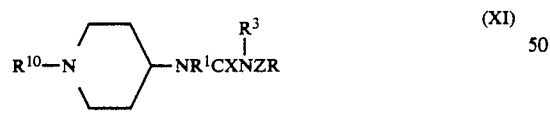

wherein $R^{10}$, $R^3$, $R^1$ and R are as herein defined and X is =O or =NH.

Compounds of formula I wherein Y is —O— may also be prepared by reacting a compound of formula

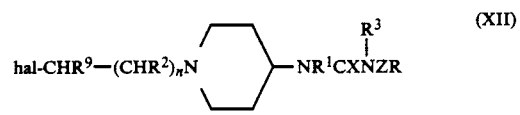

wherein hal represents halogen and the dotted line R, $R^1$, $R^2$, $R^3$, $R^9$, n, X and Z are as hereinbefore defined with a compound of formula ArOH (XIII)

wherein Ar is as hereinbefore defined. This reaction is conveniently carried out by heating reactants in an inert solvent such as dimethylsulphoxide, in the presence of base, e.g. sodium hydride. Preferably hal represents bromine or chlorine.

Yet a further process for preparing compounds of formula I wherein X is NH and the dotted line is absent, comprises reacting a compound of formula

wherein R, and $R^3$ are as hereinbefore defined with a compound of formula IV as hereinbefore defined. This reaction may be carried out in an inert solvent e.g. toluene with heating.

Once a compound of formula I having a reactive substituent group has been prepared then that compound may be converted in known manner to other compounds of formula I. For example when Ar is a group having a lower alkoxy or aryl lower alkoxy substituent on an aromatic ring dealkylation produces a corresponding compound of formula I wherein Ar carries a hydroxy substituent. When Ar is a group having nitro on an aromatic ring then reduction (e.g. catalytic hydrogenation) can convert the nitro group to an amino group. Such amino groups may be acylated.

The aforementioned processes may also include the step of conversion of an acid addition salt into the free base form or vice versa. Quaternisation of the tertiary nitrogen of the piperidine ring may be included as an optional after step, e.g. using alkyl or aryl lower alkyl halides, e.g. methyl iodide, benzyl chloride.

Starting materials used in the above mentioned processes are known compounds or may be prepared by analogous processes. For example, a compound of formula II wherein X=O may be prepared by reducing the corresponding compound of formula (XIV)

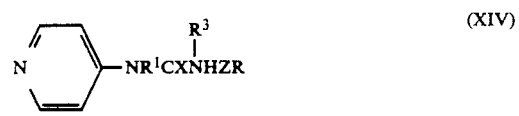

using for example catalytic hydrogenation. Compounds of formula XIV wherein $R^3$ is H and X is O or S may be prepared by reacting a 4-aminopyridine with a compound of formula RZNCX. Compounds of formula I or XIV wherein Z is —CO— and $R^3$ is lower alkyl may be prepared by alkylating a corresponding compound of formula I or XIV wherein $R^3$ is hydrogen (e.g. using an alkali metal hydride and an alkyl halide).

Compounds of formula VIII may be prepared by reacting a compound of formula III wherein W is halogen, especially bromine, with a compound of formula XIV.

Two general reactions for preparing starting materials of formula II are illustrated in the scheme below:

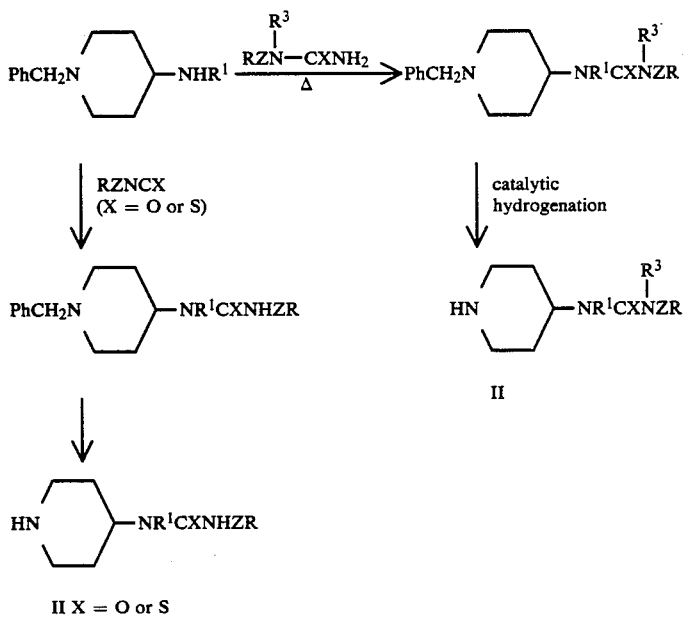

II X = O or S

If necessary, in any of the reactions herein described, reactive substituent groups may be blocked during a reaction and released at a later stage. For example an amino substituent may be protected by a benzyloxy-carbonyl group which is removable using $H_2/Pd$ at the end of a reaction. Dehydropiperidine compounds of formula I (in which the optional bond is present) are also useful as intermediates for preparing the piperidines of formula I, being converted by reduction. Acylurea compounds of formula I are also useful as intermediates for preparing other acylurea compounds of formula I, by hydrolysing to give the urea of formula VI and re-acylating.

This invention also includes pharmaceutical compositions containing as active ingredient an active compound of formula I as above defined. The active compound may be finely comminuted if desired. In addition to the active ingredient, the compositions also contain a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10-80% of the active ingredient.

Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances composition can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances, a compound is orally active and can be administered orally either in liquid or solid composition form.

Preferably the pharmaceutical composition is in unit dosage form. In such form, the composition is subdivided in unit doses containing appropriate quantities of the active ingredients; the unit dosage form can be a packaged composition, the package containing specific quantities of composition, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg or less to 500 or more, according to the particular need and the activity of the active ingredient. The invention also includes the compounds in the absence of carrier where the compounds are in unit dosage form.

A further aspect of this invention includes a method of alleviating depression in a warm blooded animal afflicted with depression, which method comprises administering to said animal an effective amount of a compound of formula I as defined above.

The amount of compound used will depend on the compound employed, the severity and nature of the depression and the animal being treated. With large animals (about 70 kg body weight) by the oral route the dose is preferably from about 5 to about 75 mg and most preferably from about 10 to about 25 mg every four hours or as needed. By the parenteral route the dosage is preferably from about 2 to about 35 mg as needed. Ideally therapy should be initiated with lower dosages, the dosage thereafter being increased until the desired anti-depressive effect is obtained.

A further aspect of this invention provides chemical intermediates for the compounds of formula I which intermediates have the formula VI as hereinbefore defined wherein $R^3$ is hydrogen, and formula VIII as hereinbefore defined.

The following examples illustrate the invention:

EXAMPLE 1

1-Benzoyl-3-[1-(naphth-2-ylmethyl)piperid-4-yl]urea

4-Benzoylureidopiperidine (1.28 g, 0.005 m), 2-(bromomethyl)naphthalene (1.1 g, 0.005 m) and triethylamine (0.6 g, 0.006 m) in dimethylformamide (25 cm$^3$) were stirred at room temperature for 23 hours. Water was added and the precipitated solid filtered off and washed well with water. The solid was suspended in warm ethanol, acidified with ethanolic HCl and then heated until all the solid had dissolved. The title compound crystallised and was collected as the hydrochloride salt, hemihydrate (1.6 g), m.p. 232°–234° C.

Analysis: $C_{24}H_{25}N_3O_2.HCl.\frac{1}{2}H_2O$ requires: C, 66.58; H, 6.29; N, 9.70%. Found: C, 66.57; H, 6.43; N, 9.45%.

EXAMPLE 2

1-Benzoyl-3-[1-(naphth-1-ylmethyl)piperid-4-yl]urea

1-Chloromethylnaphthalene (0.88 g, 0.005 m), 4-benzoylureidopiperidine (1.28 g, 0.005 m) and triethylamine (0.6 g) in dimethylformamide (25 cm$^3$) were stirred at room temperature for 24 hours. Water was added and the precipitated solid filtered off. The solid was suspended in isopropylalcohol and acidified with ethanolic HCl. The title compound was filtered off and dried as the hydrochloride salt, hemihydrate (1.2 g), m.p. 185°–186° C.

Analysis: $C_{24}H_{25}N_3O_2.HCl.\frac{1}{2}H_2O$ requires: C, 66.58; H, 6.29; N, 9.70%. Found: C, 66.19; H, 6.52; N, 9.72%.

EXAMPLE 3

1-Benzoyl-3-[1-(4-isopropylbenzyl)piperid-4-yl]urea

4-Isopropylbenzyl chloride (0.84 g, 0.005 m), 4-benzoylureidopiperidine (1.28 g, 0.005 m) and triethylamine (0.6 g) in dimethylformamide (25 cm$^3$) were stirred at room temperature for 24 hours. Water was added and the precipitated solid filtered off. The solid was suspended in isopropylalcohol and acidified with ethanolic HCl. The title compound was filtered off and dried (1.2 g), m.p. 240°–242° C. as the hydrochloride salt, hemihydrate.

Analysis: $C_{23}H_{29}N_3O_2.HCl.\frac{1}{2}H_2O$ requires: C, 65.01; H, 7.35; N, 9.89%. Found: C, 65.24; H, 7.66; N, 9.67%.

EXAMPLE 4

1-Benzoyl-3-[1-(6-methoxynaphth-2-ylmethyl)piperid-4-yl]urea

6-Methoxynaphth-2-ylmethanol (0.94 g, 0.005 m) in dry benzene (10 cm$^3$) was refluxed with thionyl chloride (3 cm$^3$) for 3 hours. The solvent was evaporated and the residue treated with benzene (3×) and evaporated. 4-Benzoylureidopiperidine (1.28 g, 0.005 m), triethylamine (1.5 g, 0.015 m) and dimethylformamide (25 cm$^3$) was added to the residue and the reaction mixture stirred at 50° C. for 2 hours. The solution was filtered and then diluted with water. The precipitated solid was washed with water, dissolved in chloroform and the chloroform extract washed with water and dried (MgSO$_4$). Evaporation gave a solid which was suspended in ethanol, acidified with ethanolic HCl and heated until all the solid had dissolved. On cooling the title compound crystallised and was filtered and dried as the hydrochloride, hemihydrate (1.3 g), m.p. 243°–244° C.

Analysis: $C_{25}H_{27}N_3O_3.HCl.\frac{1}{2}H_2O$ requires: C, 64.85; H, 6.31; N, 9.07%. Found: C, 64.59; H, 6.40; N, 8.90%.

EXAMPLE 5

3-Benzoyl-1-[1-(1,4-benzodioxan-6-ylmethyl)piperid-4-yl]urea 1,4-Benzodioxan-6-ylmethanol (1.55 g, 9.34 mmol) and thionyl chloride (1.7 g, 14.29 mmol) were refluxed in sodium-dried diethyl ether (30 cm$^3$) for 3 hours then the solvent and excess thionyl chloride evaporated. The residue was dissolved in toluene (20 cm$^3$), thionyl chloride (1.7 g, 14.29 mmol) was added and the solution heated and stirred at 80° C. for 3 hours. Evaporation of the solvent gave a residue. 4-Benzoylureidopiperidine (2.0 g, 8.1 mmol) and triethylamine (1.09 g, 10 mmol) were added to the residue and refluxed in isopropyl alcohol overnight. The isopropyl alcohol was evaporated and the residue triturated with water. The water was decanted and the residue crystallised from isopropyl alcohol (1.64 g).

The base was suspended in refluxing isopropyl alcohol, ethanolic HCl was added and the mixture filtered. The filtrate was cooled at 5° C. overnight and the title compound collected and dried as the hydrochloride, quarterhydrate (1.46 g), m.p. 231°–235° C.

Analysis: $C_{22}H_{25}N_3O_4.HCl.\frac{1}{4}H_2O$ requires: C, 60.55; H, 6.12; N, 9.63%. Found: C, 60.74; H, 6.27; N, 9.38%.

EXAMPLE 6

1-Benzoyl-3-[1-(3,4-dimethylbenzyl)piperid-4-yl]urea 3,4-Dimethylbenzyl alcohol (0.68 g, 0.005 m) in dry benzene (10 cm$^3$) was treated with thionyl chloride (3 cm$^3$) and refluxed for 3 hours. The solvent was evaporated and the residue treated with benzene (3 times) and evaporated. 4-Benzoylureidopiperidine (1.28 g, 0.05 m), triethylamine (1.5 g, 0.015 m) and dimethylformamide (25 cm$^3$) were added to the residue and the reaction mixture stirred at 50° C. for 2 hours. The solution was filtered and the filtrate diluted with water. The precipitated solid was filtered, dissolved in chloroform and washed well with water, dried (MgSO$_4$) and evaporated to give a solid. The solid was suspended in ethanol and acidified with ethanolic HCl to give the title compound, which was recrystallised from ethanol as the hydrochloride, quarterhydrate, m.p. 239°–240° C.

Analysis: $C_{22}H_{27}N_3O_2.HCl.\frac{1}{4}H_2O$ requires: C, 65.01; H, 7.07; N, 10.34%. Found: C, 64.62; H, 7.05; N, 10.15%.

EXAMPLE 7

1-Benzoyl-3-[1-(3-aminobenzyl)piperid-4-yl]urea

1-Benzoyl-3-[1-(3-nitrobenzyl)piperid-4-yl]urea 4.47 g (from Example 13) was hydrogenated with 5% Pd/C (0.5 g) at atmospheric pressure and room temperature until no more hydrogen was taken up. The catalyst was filtered and the filtrate evaporated. The residue was dissolved in water and basified with 0.880 ammonia. The precipitated solid was filtered, washed well with water, dried, treated with charcoal, and evaporated to give the title compound, (1.9 gms). This was recrystallised from ethanolic HCl to give the dihydrochloride salt, monohydrate, m.p. 194°–195° C.

EXAMPLE 8

1-Benzoyl-3-[1-(3-dimethanesulphonylaminobenzyl)-piperid-4-yl]urea

Methanesulphonyl chloride (0.55 g) was added at room temperature to a stirred solution of the product of Example 7 (1.69 g) and triethylamine (0.5 g) in chloroform (10 cm³). After addition was complete the solution was allowed to stir for 3 hours, then washed with water, dried, and evaporated. The residue was purified by trituration with ethanol at reflux. The product was suspended in ethanol, acidified with ethanolic HCl, heated for 5 minutes, cooled, and the title hydrochloride collected by filtration (0.5 g), m.p. 189°–91° C.

Analysis: $C_{22}H_{28}N_4O_6S_2.HCl.\frac{1}{2}H_2O$ requires: C, 47.69; H, 5.46; N, 10.11%. Found: C, 47.56; H, 5.25; N, 9.74%.

EXAMPLES 9 TO 35

Using the procedure of Example 1 the following compound of formula I are obtained by reacting the appropriate compound of formula III wherein W is chlorine or bromine with 4-benzoylureidopiperidine:

| Example No. | Compound |
|---|---|
| 9. | 1-Benzoyl-3-[-(2-[naphth-1-yloxy]ethyl)-piperid-4-yl]urea (m.p. of HCl, quarterhydrate salt = 226–229° C.). |
| 10. | 1-Benzoyl-3-[1-(3,4-dichlorobenzyl)-piperid-4-yl]urea (m.p. of HCl, hemihydrate salt = 244–245° C.). |
| 11. | 1-Benzoyl-3-[1-(4-t-butylbenzyl)piperid-4-yl]urea, (m.p. of HCl, quarterhydrate salt = 202–204° C.). |
| 12. | 1-Benzoyl-3-[1-(4-n-butoxybenzyl)-piperid-4-yl]urea, (m.p. of HCl, hemihydrate salt = 214–217° C.). |
| 13. | 1-Benzoyl-3-[1-(3-nitrobenzyl)piperid-4-yl]urea, (m.p. of HCl, quarterhydrate salt = 255–257° C.). |
| 14. | 1-Benzoyl-3-[1-(5,6,7,8-tetrahydro-naphth-2-ylmethyl)piperid-4-yl]urea (m.p. of HCl salt = 233–5° C.). |
| 15. | 1-Benzoyl-3-[1-(4-ethylbenzyl)piperid-4-yl]urea, (m.p. of HCl salt = 234–236° C.). |
| 16. | 1-Benzoyl-3-[1-(3,4-dibromobenzyl)-piperid-4-yl]urea, (m.p. of HCl salt = 228–230° C.). |
| 17. | 1-Benzoyl-3-[1-(2,5-dimethylbenzyl)-piperid-4-yl]urea, (m.p. of HCl salt = 231–232° C.). |
| 18. | 1-Benzoyl-3-[1-(4-n-propoxybenzyl)-piperid-4-yl]urea, (m.p. of HCl salt = 232–234° C.). |
| 19. | 1-Benzoyl-[1-[2-(naphth-2-oxy)ethyl]-piperid-4-yl]urea (m.p. of HCl salt = 215–218° C.). |
| 20. | 1-Benzoyl-3-[1-(indan-5-ylmethyl)-piperid-4-yl]urea, (m.p. of HCl salt = 253–6° C.). |
| 21. | 1-Benzoyl-3-[1-(1-(naphth-2-yl)ethyl)-piperid-4-yl]urea, (m.p. of HCl salt = 172–4° C.). |
| 22. | 1-Benzoyl-3-[1-(4-methyl-3-nitrobenzyl)-piperid-4-yl]urea, (m.p. of HCl salt = 232–234° C.). |
| 23. | 1-Benzoyl-3-[1-(3-bromo-4-methylbenzyl)-piperid-4-yl]urea. |
| 24. | 1-Benzoyl-3-[1-(quinol-4-ylmethyl)-piperid-4-yl]urea, (m.p. of sesquihydrochloride salt = 211–213° C.). |
| 25. | 1-Benzoyl-3-[1-(quinol-2-ylmethyl)-piperid-4-yl]urea, (m.p. of di-HCl salt = 213–215° C.). |
| 26. | 1-Benzoyl-3-[1-(3,5-dimethylbenzyl)-piperid-4-yl]urea, (m.p. of HCl, quarterhydrate salt = 248–252° C.). |
| 27. | 1-Benzoyl-3-[1-(2,4-dimethylbenzyl)-piperid-4-yl]urea, (m.p. of HCl, quarterhydrate salt = 230–232° C.). |
| 28. | 1-Benzoyl-3-[1-(3-bromobenzyl)piperid-4-yl]urea (m.p. of HCl, quarterhydrate salt = 222–224° C.). |
| 29. | 1-Benzoyl-3-[1-(3-iodobenzyl)piperid-4-yl]urea (m.p. of HCl salt = 217–219° C.). |
| 30. | 1-Benzoyl-3-[1-(pyrid-4-ylmethyl)-piperid-4-yl]urea (m.p. of di-HCl salt = 236–238° C.). |
| 31. | 1-Benzoyl-3-[1-(3-trifluoromethylbenzyl)-piperid-4-yl]urea (m.p. of HCl salt = 241–243° C.). |
| 32. | 1-Benzoyl-3-[1-(4-methoxycarbonyl-benzyl)piperid-4-yl]urea (m.p. of HCl salt = 247–249° C.). |
| 33. | 1-Benzoyl-3-[1-(6-methylnaphth-2-yl-methyl)piperid-3-yl]urea (m.p. of HCl, hemihydrate salt = 250–253° C.). |
| 34. | 1-Benzoyl-3-[1-(1-[benzofuran-2-yl]-ethyl)piperid-4-yl]urea (m.p. of HCl salt = 148–149° C.). |
| 35. | 1-[1-(5-Acetamido-2-hydroxybenzyl)-piperid-4-yl]-3-benzoylurea (m.p. of HCl, ¾ hydrate salt = 230–232° C.). |

EXAMPLE 36

1-Benzoyl-3-[1-(naphth-2-ylmethyl)piperid-4-yl]thiourea

4-Amino-1-(naphth-2-ylmethyl)piperidine (1.0 g, 0.0042 m) and benzoylisothiocyanate (0.69 g, 0.0042 m) in toluene (120 cm³) was stirred at room temperature for 6 hours. The solvent was evaporated and the gum dissolved in isopropyl alcohol and acidified with ethanolic HCl. The solvent was evaporated and the residue dissolved in ethyl acetate. The title compound crystallised and was filtered and dried as the monohydrochloride quarterhydrate salt, m.p. 212°–214° C.

EXAMPLE 37

1-[1-(Naphth-2-ylmethyl)piperid-4-yl]-3-(then-2-oyl)urea

4-Amino-1-(naphth-2-ylmethyl)piperidine (1.0 g, 0.0047 m) and 1-(then-2-oyl)urea (0.65 g, 0.0042 m) in pyridine (5 cm³) was refluxed for 9.5 hours. The solvent was evaporated, water added, and the precipitated title compound filtered and washed well with water. This was recrystallised from ethanol, converted to the hydrochloride salt in ethanol with ethanolic HCl, and recrystallised from ethanol, 0.5 g, at the hydrochloride, m.p. 217°–219° C.

EXAMPLE 38

1-Benzoyl-3-[1-(naphth-2-ylmethyl)piperid-4-yl]quanidine

4-Amino-1-(naphth-2-ylmethyl)piperidine (1.0 g, 0.0042 m) and benzoyl cyanamide (0.67 g, 0.0042 m) in toluene (100 cm$^3$) were refluxed for 15 hours. The solvent was evaporated and the residue recrystallised from the minimum amount of isopropyl alcohol and recrystallised twice more from ethanol to give 0.65 g of the title compound, m.p. dihydrochloride quarter hydrate, m.p. 260°–262° C.

EXAMPLES 39–42

Using a procedure analogous to Example 37 4-amino-1-(naphth-2-ylmethyl)piperidine is reacted with each of the following ureas:
3,4-dimethylbenzoylurea,
3-trifluoromethylbenzoylurea,
4-nitrobenzoylurea
and 1-(pyrid-4-oyl)urea to give the following compounds:

| Example No. | Compound |
|---|---|
| 39. | 1-(3,4-Dimethylbenzoyl)-3-[1-(naphth-2-ylmethyl)piperid-4-yl]urea (m.p. of HCl, quarterhydrate = 223–226° C.). |
| 40. | 1-(1-(Naphth-2-ylmethyl)piperid-4-yl]-3-(3-trifluoromethylbenzoyl)urea (m.p. 251–253° C.). |
| 41. | 1-[1-(Naphth-2-ylmethyl)piperid-4-yl]-3-(4-nitrobenzoyl)urea (m.p. of HCl salt = 264–5° C.). |
| 42. | (1-(Pyrid-4-oyl)-3-[1-(naphth-2-ylmethyl)piperid-4-yl]urea (m.p. 254–255° C.) |

EXAMPLE 43

1-(4-Methoxybenzoyl)-3-[1-(naphth-2-ylmethyl)piperid-4-yl]urea

1-Benzoyl-3-[1-(naphth-2-ylmethyl)piperid-4-yl]urea (prepared according to Example 1) is hydrolysed by refluxing in 2N sodium hydroxide to give [1-(naphth-2-ylmethyl)piperid-4-yl]urea (m.p. 183°–5° C.). The product is acylated by reaction with 4-methoxybenzoyl chloride to give the title compound, m.p. of HCl, quarterhydrate=193°–193.5° C.).

EXAMPLES 44–45

In a manner analogous to Example 1,2-bromomethylnaphthalene was reacted with the following compounds of formula II:
4-benzylureidopiperidine,
4-(p-fluorobenzoyl)ureidopiperidine
to give the following compounds of formula I:

| Example No. | Compound |
|---|---|
| 44. | 1-Benzyl-3-[1-naphth-2-ylmethyl)piperid-4-yl]urea (m.p. of HCl, ¼ hydrate salt = 243–247° C. (dec)). |
| 45. | 1-(p-Fluorobenzoyl)-3-[1-(naphth-2-ylmethyl)piperid-4-yl]urea (m.p. of HCl, ¼ hydrate salt = 242–245° C. (dec)). |

EXAMPLES 46–54

Using a procedure analogous to Example 1,4-benzoylureidopiperidine is reacted with the following compounds:
2-(naphth-2-yl)ethyl tosylate,
6-cyanonaphth-2-ylmethyl bromide,
6-fluoronaphth-2-ylmethyl bromide,
6-bromonaphth-2-ylmethyl bromide,
1-(naphth-2-yl)propyl chloride,
di-(naphth-2-ylmethyl)sulphate,
6-chloromethylquinoxaline,
3-chloromethylcinnoline,
6-chloromethylisoquinoline,
to give the following compounds

| Example No. | Compound |
|---|---|
| 46. | 1-Benzoyl-3-[1-(2-[naphth-2-yl]ethyl)piperid-4-yl]urea, (m.p. of HCl salt = 230–232° C.). |
| 47. | 1-Benzoyl-3-[1-(6-cyanonaphth-2-ylmethyl)piperid-4-yl]urea, (m.p. of HCl, hemihydrate salt = 264–266° C.). |
| 48. | 1-Benzoyl-3-[1-(6-fluoronaphth-2-ylmethyl)piperid-4-yl]urea. |
| 49. | 1-Benzoyl-3-[1-(6-bromonaphth-2-ylmethyl)piperid-4-yl]urea. |
| 50. | 1-Benzoyl-3-[1-[1-(naphth-2-yl)propyl]piperid-4-yl]urea. |
| 51. | 1-Benzoyl-3-[1-(naphth-2-ylmethyl)piperid-4-yl]urea, m.p. of HCl, hemihydrate salt = 232°–234° C.). |
| 52. | 1-Benzoyl-3-[1-(quinoxalin-6-ylmethyl)piperid-4-yl]urea. |
| 53. | 1-Benzoyl-3-[1-(cinnolin-3-ylmethyl)piperid-4-yl]urea. |
| 54. | 1-Benzoyl-3-[1-(isoquinolin-6-ylmethyl)piperid-4-yl]urea. |

EXAMPLE 55

1-Benzoyl-3-[1-(naphth-2-ylmethyl)piperid-4-yl]urea

2-Bromomethylnaphthalene is heated with 4-benzoylureidopyridine in acetonitrile solvent to give 1-benzoyl-3-[1-(naphth-2-ylmethyl)-4-pyridinium urea bromide m.p. 247°–8° C. This compound is reduced by refluxing with sodium borohydride in isopropyl alcohol solvent to give the title compound, m.p. of HCl hemihydrate salt=232°–234° C.

Alternatively 1-benzoyl-3-[1-(naphth-2-ylmethyl)-4-pyridinium]urea bromide is reduced with sodium borohydride in methanol solvent to give 1-benzoyl-3-[1-(naphth-2-ylmethyl)-3,4-dehydropiperid-4-yl]urea. This compound may then be reduced by refluxing with sodium borohydride in isopropyl alcohol to give the title compound.

EXAMPLE 56

1-Benzoyl-1-methyl-3-[1-(naphth-2-ylmethyl)piperid-4-yl]urea

1-Methyl-3-[1-(naphth-2-ylmethyl)piperid-4-yl]urea (1.4 g.) (prepared by reacting 4-amino-1-(naphth-2-ylmethyl)piperidine with methyl isocyanate) in toluene (30 cm$^3$) was acylated using benzoyl chloride (0.92 g) in presence of pyridine (0.6 g) to give the title compound: m.p. of HCl, hemihydrate salt=164°–166° C.

Analysis: Found: C 67.37; H, 6.58; N, 9.45; $C_{25}H_{27}N_3O_2 \cdot HCl \tfrac{1}{2}H_2O$ requires C 67.18; H, 6.54; N, 9.40%.

EXAMPLE 57

1-Benzoyl-3-methyl-3-[1-(naphth-2-ylmethyl)piperid-4-yl]urea

Using a procedure analogous to Example 37, 4-methylamino-1-(naphth-2-ylmethyl)piperidine was reacted with benzoylurea to give the title compound. m.p. of HCl, quarterhydrate=207°-209° C.

EXAMPLE 58

N-[[[1-(2-Naphthalenylmethyl)-4-piperidinyl]amino]-carbonyl]-2-furancarboxamide

4-Amino-1-(naphth-2-ylmethyl)piperidine (1.2 g, 0.005 m) and 2-furoylurea (0.7 g) in pyridine (5 ml) was refluxed for 6 hours, then cooled. Water was added and the precipitate collected by filtration. The solid was dissolved in chloroform with a little methanol and filtered. The solvent was removed under reduced pressure and the residue was purified by medium pressure liquid chromatography on silica using $CHCl_3$: MeOH (9:1 v/v) as eluent. The isolated product (1st component eluted) was dissolved in ethyl acetate and acidified with ethanolic HCl to give a precipitate. This was filtered and dried to give 0.3 g of the title compound as the HCl, $\frac{3}{4}$ $H_2O$ salt, mp. 157°-159° C.

Analysis: Found: C61.95, H 6.02, N,9.00% $C_{22}H_{23}N_3O_3.HCl.\frac{3}{4}H_2O$ requires C,61.82, H, 6.01, N, 9.83.

EXAMPLE 59

1-(pyrid-3-oyl)-3-[1-(naphth-2-ylmethyl)piperid-4-yl]-urea

A suspension of the 4-amino-1-(naphth-2-ylmethyl)-piperidine, hydrochloride (1.65 g, 5.97 mmol) and nicotinoylurea (0.82 g, 5 mmol) in pyridine (12 cm³) was stirred and refluxed for 5 hours then triethylamine was added dropwise until a solution was formed. Heating was continued for 1 hour then the solution was allowed to cool to room temperature overnight. On the next day the mixture was heated until homogeneous then diluted with water, cooled in ice and the precipitate solid collected and sucked dry on the sinter.

The solid was suspended in boiling ethanol and ethanolic HCl was added to give an acidic solution. On cooling a gum deposited which was separated by decantation and put to one side. The supernatant solution crystallised on further cooling and the deposited solid was collected and recrystallised from ethanol containing a little methanol to give a first crop of the title compound.

The gum obtained above was triturated with warm ethanol until crystalline then the solid was recrystallised from ethanol containing a little methanol. The sample was dissolved in methanol, treated with decolourising charcoal in the usual manner, then recovered by evaporation. The glassy residue was recrystallised from ethanol and the product combined with the first crop obtained above to give the title compound as the dihydrochloride salt, mp=205°-7° C.

Analysis: Found: C 60.23; H, 5.87; N, 12.09% $C_{23}H_{24}N_4O_2.2HCl$ requires C 59.87; H, 5.68; N 12.14%.

EXAMPLE 60

N-[[[1-(6-Quinolinylmethyl)-4-piperidinyl]amino]carbonyl]benzamide

A mixture of 6-bromomethylquinoline HBr (1.4 g, 4.59 mmol), 4-benzoylureidopiperidine (1.14 g, 4.62 mmol), triethylamine (1.2 g, 11.88 mmol) and dry DMF (15 ml) was prepared at 0° C. The mixture was stirred for 0.5 hours at 0° C. then at room temperature overnight. More 6-bromomethyquinoline (0.3 g, 0.98 mmol) was added and stirring continued for 5.5 hours. The mixture was diluted with water (20 ml) and cooled in ice to give a solid which was collected, washed with water and dried. The solid was suspended in boiling ethanol (15 ml) and ethanolic HCl added to give an acidic solution which rapidly crystallised. This was cooled in ice, the solid collected, and dried to give the title compound as the dihydrochloride, ethanolate quarterhydrate salt (1.22 g,) mp 242°-4° C., phase change ca 204° C.

Analysis: Found: C 58.60, H, 6.34, N 11.28% $C_{23}H_{24}N_4O_2.2HCl.EtOH.\frac{1}{4}H_2O$ requires C, 58.65; H,6.4; N, 10.94.

EXAMPLE 61

1-(pyrid-2-oyl)-3-[1-(naphth-2-ylmethyl)piperid-4-yl]urea

Sodium (0.1 g, 4.35 mmol) in liquid ammonia (100-150 cm³) was stirred until the blue colour was discharged. A bomb was charged with [1-(naphth-2-ylmethyl)piperid-4-yl]urea (0.83 g, 2.93 mmol) and the liquid ammonia solution was added. The mixture was stirred at room temperature for 2 days then the bomb was cooled to $-78°$ C., and ethyl picolinate (0.6 g, 3.97 mmol) was added. Stirring was continued for 3 hours at room temperature then the ammonia was allowed to evaporate and the gummy residue triturated with water then ethyl acetate. The ethyl acetate suspension was filtered to give recovered [1-(naphth-2-ylmethyl)piperid-4-yl]urea (0.33 g). The filtrate was evaporated and the residue chromatographed on silica eluting with chloroform then chloroform: ethyl acetate 4:1 to give the title compound (0.37 g).

Analysis: Found: C 71.37; H, 6.33; N, 14.07% $C_{23}H_{24}N_4O_2$ requires C. 71.11, H, 6.23, N, 14.42%.

EXAMPLE 62

N[[[1-[(6-Fluoro-2-naphthalenyl)methyl]-4-piperidinyl]amino]carbonyl]-3-pyridinecarboxamide A solution of 2-bromomethyl-6-fluoronaphthalene (99 g) in dimethylformamide (400 ml) was added over 1 hour to a stirred suspension N-[[[4-piperidinyl]amino]-carbonyl-3-pyridinecarboxamide (102.5 g) in dimethylformamide (1000 ml) and diisopropylethylamine (72 ml). After stirring for a further hour the reaction was diluted with water and the precipitated product collected, washed with water, then ether and dried to give 132 g (78.5%). The base was dissolved in chloroform (700 ml) and added to a solution of maleate acid (40 g) in ethanol (400 ml) to precipitate the maleate salt of the title compound 142 g (65.8%) m.p. 206°-207° C.

Analysis $C_{23}H_{23}N_4FO_2.C_4H_4O_4$ requires: C, 62.1; H, 5.2; N, 10.7% Found: C, 61.7; H,5.2; N, 10.6%

EXAMPLE 63

N-[[[1-[(6-Fluoro-2-naphthalenyl)methyl]-4-piperidinyl]amino]carbonyl]-4-pyridinecarboxamide A mixture of 4-amino-1-[(6-fluoro-2-naphthalenyl)-methyl]piperidine (1.3 g, 5 mmol), 4-pyridoylurea (0.9 g, 5 mmol) and pyridine (6 ml) was stirred at reflux for 16 hours. The solution was diluted with water (8 ml)

and the precipitated dark brown product collected by filtration to give 1.5 g. The crude product was dissolved in chloroform (25 ml), shaken with decolourising charcoal, filtered and evaporated. The residue was suspended in hot ethanol (20 ml) and succinic acid (0.44 g) added to give a clear solution which crystallised on standing. The product crystals were collected by filtration and washed with ethanol to give the succinate salt of the title compound. m.p. 187°–188° C.

Analysis $C_{23}H_{23}N_4FO_2.C_4H_6O_4$ requires: C, 61.82; H, 5.57; N, 10.68% Found: C, 61.89; H, 5.66; N, 10.51%

EXAMPLE 64

The compound of example 62 when in the form of the free base has an m.p. 199°–200° C. The citrate salt has an m.p. 141°–142° C. The monohydrochloride ¾ $H_2O$ salt has an m.p. 242°–244° C.

EXAMPLE 65

3-Methoxy-N-[[[1-(2-quinolinylmethyl)-4-piperidinyl]amino]carbonyl]benzamide 2-(2-Chloromethyl)quinoline hydrochloride (0.642 g, 3 mmol) was added to a stirred solution of 3-methoxy-N-[[[4-piperidinyl]amino]carbonyl]benzamide (0.832 g, 3 mmol), and triethylamine (1.25 cm$^3$, 9 mmol) in dimethylformamide (6 cm$^3$) maintained at 70° C. Heating and stirring were maintained for a further 1 hour. The mixture was then cooled and diluted with water to precipitate a gum. The product solidified on standing/stirring and was collected, washed with water, and crystallised twice from ethanol to give the title compound 0.8 g (63.7%). This was suspended in hot ethanol and acidified with ethanolic hydrogen chloride to precipitate the hydrochloride salt of the title compound. Partial loss of HCl occurred on drying at 100° C. under vacuum and the title compound was finally obtained as a one and one half hydrochloride 0.75 g (52.8%) m.p. 208°–11° C.

Analysis $C_{24}H_{26}N_4O_3 \cdot 1\tfrac{1}{2}$ HCl requires: C, 60.92; H, 5.86; N, 11.84; Cl, 11.24% Found: C, 60.68; H, 5.80; N, 11.97; Cl 10.35%

EXAMPLE 66

N-[[[1-(6-Quinolinylmethyl)-4-piperidinyl]amino]carbonyl]3-pyridinecarboxamide

4-Amino-1-(quinol-6-ylmethyl)piperidine(1.3 g 5.4 mmol) and nicotinoylurea (0.6 g, 3.64 mmol) were refluxed vigorously in pyridine (2 ml) for 4.5 hours. The solution was cooled and diluted with ethyl acetate, the precipitated solid was collected and washed well with ethyl acetate to give 1.08 g of a solid. This was chromatographed on a short silica column eluting with chloroform methanol (9:1 v/v) to give 0.89 g of the title compound, mp 196°–8° C.

Analysis $C_{22}H_{23}N_5O_2$ requires: C, 67.85; H, 5.95; N 17.98. Found: C, 67.89; H, 5.86; N, 17.85%

We claim:

1. A compound of the formula:

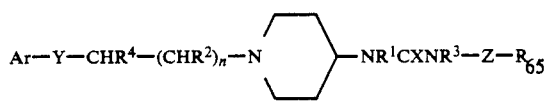

wherein n is 0 or 1;

$R^1$, $R^2$, $R^3$ and $R^4$ are independently hydrogen or $C_1$-$C_4$ alkyl;

X is =O or =S;

Y is —O— or a direct bond;

Z is —CO— or —CH$_2$—;

R is 2, 3 or 4-pyridyl or 2, 3 or 4-pyridyl substituted by one or two substituents selected from $C_1$-$C_4$ alkyl, $C_1$-$C_4$ alkoxy, hydroxy, fluoro, chloro, bromo, chloroethyl, trifluoromethyl, and nitro, and;

Ar is 2, 4, 5 or 6-quinolinyl or 2,4,5 or 6-quinolinyl substituted by one or two substituents selected from $C_1$-$C_4$alkyl, $C_1$-$C_4$alkoxy, hydroxy, fluoro, chloro, bromo, chloroethyl, trifluoromethyl, amino, $C_1$-$C_4$alkylamino, di-($C_1$-$C_4$alkyl)amino, $C_1$-$C_4$alkylcarbonylamino, dimethane or diethanesulphonylamino, nitro or cyano, or a pharmaceutically acceptable acid addition or quaternary ammonium salt thereof, in which the dotted line represents an optional double bond.

2. A compound of claim 1 in which Y is a direct bond.

3. A compound of claim 1 in which Z is —CO—.

4. A compound of claim 1 in which Ar is 2- or 6-quinolinyl.

5. A compound of claim 1 in which R is 2, 3 or 4-pyridyl.

6. A compound of claim 1 in which R is 3-pyridyl.

7. A compound of claim 1 which is N-[[[1-(6-quinolinylmethyl)-4-piperidinyl]amino]carbonyl]-3-pyridinecarboxamide, or a pharmaceutically acceptable acid addition or quaternary ammonium salt thereof.

8. A pharmaceutical composition comprising an amount effective to alleviate depression of a compound of claim 1 or a pharmaceutically acceptable acid addition or quaternary ammonium salt thereof and a pharmaceutically acceptable carrier.

9. A compound of the formula:

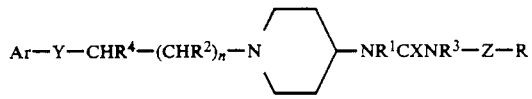

wherein $R^1$, $R^2$, $R^3$ and $R^4$ are independently hydrogen or $C_1$-$C_4$ alkyl;

X is =O or =S;

Y is —O— or a direct bond;

Z is —CO— or —CH$_2$—;

R is 2, 3 or 4-pyridyl or 2, 3 or 4-pyridyl substituted by one or two substituents selected from $C_1$-$C_4$ alkyl, $C_1$-$C_4$ alkoxy, hydroxy, fluoro, chloro, bromo, chloroethyl, trifluoromethyl, and nitro, and;

Ar is 3, 4, 5 or 6-isoquinolinyl or 3,4,5 or 6-isoquinolinyl substituted by one or two substituents selected from $C_1$-$C_4$alkyl, $C_1$-$C_4$alkoxy, hydroxy, fluoro, chloro, bromo, chloroethyl, trifluoromethyl, amino, $C_1$-$C_4$alkylamino, di-($C_1$-$C_4$alkyl)amino, $C_1$-$C_4$alkylcarbonylamino, dimethane or diethanesulphonylamino, nitro or cyano, or a pharmaceutically acceptable acid addition or quaternary ammonium salt thereof, in which the dotted line represents an optional double bond.

10. A compound of claim 1 in which Y is a direct bond.

11. A compound of claim 1 in which Z is —CO—.

12. A compound of claim 1 in which Ar is 3- or 6-isoquinolinyl.

13. A compound of claim 1 in which R is 2, 3 or 4-pyridyl.

14. A compound of claim 1 in which R is 3-pyridyl.

15. A pharmaceutical composition comprising an amount effective to alleviate depression of a compound of claim 9 or a pharmaceutically acceptable acid addition or quaternary ammonium salt thereof and a pharmaceutically acceptable carrier.

16. A method for alleviating depression in a mammal afflicted with depression, which comprises administering to said mammal an amount effective to alleviate depression of a compound of the formula

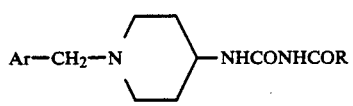

wherein
R is 3 or 4-pyridyl; and
Ar is unsubstituted-6-quinolinyl, unsubstituted-6-isoquinolinyl, or 2-quinolinyl or 3-isoquinolinyl which may be substituted at the 6 and/or 7 position by one or two substituents selected from methyl, ethyl, propyl, isopropyl, fluoro or chloro, or
a pharmaceutically acceptable acid addition or quaternary ammonium salt thereof, in which the dotted line represents an option double bond.

17. A method of claim 16 in which R is 3-pyridyl.

18. A method of claim 16 in which Ar is 6-quinolinyl or 6-isoquinoliny.

19. A method of claim 16 in which Ar is 2-quinolinyl or 3-isoquinolinyl unsubstituted or substituted at the 6 and/or 7 position with fluoro.

20. A method of claim 16 in which the given compound of the formula is N-[[[1-(6-quinolinylmethyl)-4-piperidinyl]amino]carbonyl]-3-pyridinecarboxamide or a pharmaceutically acceptable acid addition or quaternary ammonium salt thereof.

* * * * *